(12) United States Patent
Salz et al.

(10) Patent No.: US 6,450,717 B1
(45) Date of Patent: Sep. 17, 2002

(54) APPLICATOR AND METHOD OF APPLYING

(75) Inventors: Ulrich Salz, Lindau (DE); Andre Rumphorst, Vaduz (LI); Alexandros Gianasmidis, Heerbrugg (CH); Frank Muller, Feldkirch (AT); Volker Rheinberger, Liechtenstein (LI)

(73) Assignee: Ivoclar AG., Schaan (LI)

( * ) Notice: Subject to any disclaimer, the term of this patent is extended or adjusted under 35 U.S.C. 154(b) by 0 days.

(21) Appl. No.: 09/695,029

(22) Filed: Oct. 24, 2000

Related U.S. Application Data

(60) Provisional application No. 60/177,931, filed on Jan. 25, 2000.

(30) Foreign Application Priority Data

Nov. 25, 1999 (DE) .......................... 199 56 705

(51) Int. Cl.[7] .............................. A46B 11/00; A61C 3/00
(52) U.S. Cl. ...................... 401/125; 206/63.5; 401/129; 401/130; 433/89; 433/226
(58) Field of Search ................ 401/129, 127, 401/126, 125, 118, 130; 206/63.5, 209, 368, 362.3, 15.3; 433/77, 89, 226

(56) References Cited

U.S. PATENT DOCUMENTS

| | | | |
|---|---|---|---|
| 5,324,126 A | | 6/1994 | Gueret |
| 5,492,426 A | * | 2/1996 | Gueret .................. 401/130 X |
| 5,525,647 A | * | 6/1996 | Eichmiller ............... 433/89 X |
| 5,573,340 A | * | 11/1996 | Gueret .................. 401/130 X |
| 6,202,897 B1 | * | 3/2001 | Martin et al. ............. 433/90 X |

FOREIGN PATENT DOCUMENTS

| | | |
|---|---|---|
| DE | 1 960 074 | 6/1971 |
| DE | 2 024 402 | 12/1971 |

* cited by examiner

Primary Examiner—David J. Walczak
Assistant Examiner—Kathleen J. Prunner
(74) Attorney, Agent, or Firm—Alan S. Korman; John C. Thompson

(57) ABSTRACT

An applicator kit, for dental purposes. has an application element with a grip area for handling, and also has a shaft, on a tip of which is disposed an application member, preferably in the form of a micro-brush that is provided with a reaction substance. A cup shaped sealing mechanism surrounds the shaft and the application member. The cup shaped sealing mechanism is slidably received within a housing which also receives a low velocity fluid initially spaced away from the cup-shaped sealing mechanism. The reaction substance on the application member is activated by pressing the sealing mechanism and application member into the fluid within the housing which causes the fluid to wet the application member.

19 Claims, 4 Drawing Sheets

APPLICATOR AND METHOD OF APPLYING

This application claims benefit of provisional application No. 60/177,931.

BACKGROUND OF THE INVENTION

The present invention relates to an applicator kit, as well as to a method of applying a substance for dental purposes. The applicator kit includes an application element having a grip area and a working end. An application member is disposed at the working end and is provided with at least one reaction substance, especially with at least one catalyst.

An applicator of this type is known from U.S. Pat. No. 5,324,128. With this applicator, an application member is accommodated in a case having holes on the side via which a fluid can enter that serves for wetting the application member.

This approach is intended to prevent the fluid from escaping if the applicator is, for example, tipped over. For this purpose, sealing surfaces are provided between the case and the application element.

Such an approach may work with cosmetic products. However, in the dental area a precise introduction of an application element is critical. Even if with U.S. Pat. No. 5,324,128 relatively small holes are provided in the case, with which a certain amount of protection is intended, this cannot preclude the fluid from accidentally penetrating and hence wetting the application element already prior to the actual process of using the same.

Numerous other applicators are also know. For example, it has been proposed to maintain an application element immersed in a liquid, and by pressing down the container for this liquid to allow a further liquid to flow in the manner of an overflow in order to prepare the mixture that is to be applied. Since this approach requires two separate sealing systems, a considerable expense is required. In addition a number of sealing bands or the like means a correspondingly great susceptibility and storage instability.

In this connection, is as furthermore known to accommodate the liquids in two chambers that are separated by a membrane that is precisely destroyed by a spike that can be activated by pressing an inner housing in. This approach, however, requires a special configuration of the spike to reliably prevent the spike from colliding with the application element.

It is furthermore known to mix reactive substances, such as a composite for tooth fillings, on a base that is coated with a peroxide, or to mix the composite with a peroxide-coated spatula. This mixing has the drawback that a homogeneous mixing is not possible since it cannot be recognized when the peroxide has been completely consumed by the relatively viscous material.

It is therefore an object of the present invention to provide an applicator kit of the aforementioned general type that is economical to produce and that enables an improved handling relative to the state of the art yet provides a good storage stability, whereby in particular a homogeneous mixing of a fluid should be possible and an ease of operation together with a saving in time should be achieved.

SUMMARY OF THE INVENTION

The applicator kit of the present invention is characterized primarily in that the application element is comprised of a deformable material, especially an elastically deformable material, wherein the application member serves for receiving the reaction substance in solid, liquid or semisolid form, with which a low viscosity fluid can be activated.

Pursuant to the present invention, the application member, in other words, for example, one end of the application element, is first provided with one or more reaction substances. For example, a double catalyst system as a salt can be applied.

The inventive application element is then immersed in a liquid, for example a dental adhesive, that accompanied by the formation of a drop surrounds the application member. The application element is then introduced into the mouth of the patient, and during the actual application process the adhesive is mixed into a cavity or upon a dentine or enamel surface with the catalyst. The catalysts that might be present in the adhesive react with the catalysts of the application member, and the entire mass hardens or sets. It is also conceivable to place only a single catalyst on the application member that, for example, increases or reduces the viscosity of the adhesive.

It is particularly expedient pursuant to the present invention that the application of the adhesive to the application surface particularly promotes even obviously chemical reactions. Due to the distribution of the adhesive, even the salt present on the application member as reaction substance is well released, so that the self hardening process is enhanced. In this connection, pursuant to the present invention it is particularly expedient that the applicator kit eliminates the necessity for light hardening of the applied adhesive. Thus an entire process step, for example during introduction of an inlay or during fastening of a crown, is eliminated.

Pursuant to the present invention, the application element comprises a deformable material. In this context, "deformable" means a material hardness that is suitable for the application.

Thus, for example, the applicator can comprise a polymeric material, with the application member extending essentially in the form of a small rod to a working end. At this end, the inventive application member is provided, which is either monolithic, in other words comprises the same material as the rest of the application element, or is comprised of some other material. For example, the material for the application member can be a textile, brush hairs, a sponge, fibers, polymeric material, hard or laminated paper, or wood, with the configuration of a micro-brush being preferred. In addition, it is preferable that the material of the application member be significantly softer than dentine and tooth enamel in order during application not to have to worry about any damage to the tooth.

Pursuant to the present invention it is particularly important to have the viscosity of the liquid or fluid in the range of 10 to 500,000 mPa, especially 1,000 to 100,000 mPa, and preferably 10,000 to 50,000 mPa. The low viscosity ensures that the reaction substance will be released entirely to the application member, as has shown to be the case in tests conducted with an inventive applicator kit. The small brush hairs of a micro-brush used pursuant to one advantageous specific embodiment of the present invention evidently produce capillary effects so that with an appropriate viscosity the liquid creeps along the hairs and can directly release the reaction substance. In addition, as a liquid adhesive it enables a laminar spreading on the application surface, to which contributes the very low surface tension of the liquid.

Pursuant to the present invention, it is particularly expedient that the application member itself be provided with the reaction substance that can be activated by the liquid. The reaction can be activated by pushing in a housing that contains the fluid, or by immersion into an otherwise suitable container.

If a housing is used, it is merely necessary to provide a circumferential sealing of the sealing mechanism in order to maintain storage stability. The inventive application member is preferably provided with one or more catalysts. For this purpose, it is immersed into a benzene sulfinic acid solution and/or into an amine solution, for example diethanol-p-toluidine, and allowed to dry. The reaction substance is stored as a dry substance and is hence particularly stable. Therefore, as a reaction substance a double coating by two catalysts can also be applied, so that with the activation upon introduction of the sealing mechanism and overcoming of the sealing function by the fluid, in practice three components are brought together and react appropriately, whereby the fluid is used as adhesive for the adhesion of composite materials upon tooth enamel or dentine.

In this embodiment, the inventive applicator kit can be made available as a single-dose unit. However, in other embodiments it is also possible to separately prefabricate and package the application member, for example as an individual brush or brush comb, and to immerse it into the fluid for use. The single-dose unit or the individual or multiple brush (brush comb) can preferably be sealed in foil, for example of aluminum, or coated plastic, in order to improve the storage stability. If, for example, larger cracks are to be sealed or tooth enamel is to be applied, an adequate quantity of material can be made available in this manner.

It is particularly expedient pursuant to the present invention if the reaction substance is present in solid form. However, this is by no means absolutely necessary, since it is also possible to provide the material in semisolid or even liquid form as drops. Depending upon the type of fluid, not only a light hardening but also a self hardening adhesive can be made available.

It is particularly advantageous pursuant to the present invention to provide quite wide slots for the supply of the fluid to the application member. When the application element, in other words the seal, is strongly pushed into the housing, the fluid is pressed upwardly, accompanied by pronounced swirling, through the gap between the base of the sealing mechanism and the inner side of the housing, and flows at a quite high flow velocity into the region provided with micro hairs. As a consequence, an intensive mixing results, so that the chemical reaction is very rapidly initiated by the catalysts, and the finished adhesive is immediately ready for use. The required reaction time can, for example, be one second; the time does not generally fall below such a short time span.

To this extent, with surprisingly simple measures an applicator kit is made available that on the one hand is stable for a long time and on the other hand is rapidly usable.

Pursuant to one particularly advantageous specific embodiment to the present invention, even the sealing mechanism can be pressed down with the application element. This can be realized either with the blunt tip of the application member, or with an appropriate projection of the shaft of the application element.

It is furthermore particularly advantageous pursuant to the present invention if the application member is embodied as a micro-brush. Such a micro-brush can be produced by flocking the tip of the shaft of the application element. Within the context of the present invention, the application member means any type of application mechanism produced by applying an absorptive substance onto the shaft tip, so that even a foam type of structure could be provided.

The absorptive capacity of the micro-brush for the fluid can be adapted to the desired application volume in conformity with the hair length, in other words the type of flocking, or by other suitable measures, for example, to wet larger tooth surfaces, which correspondingly require more adhesive agent, it can be expedient to provide a micro-brush having a greater drop receiving capacity for the fluid, with the brush hairs extending to the side supports of the sealing mechanism.

Pursuant to another particularly expedient embodiment of the present invention, such an applicator can be bendable in a particularly advantageous manner. For this purpose, a constriction or narrowed portion can be provided about the shaft of the application element to permit a plastic deformation of the application element such that it can be bent after removal from the housing.

This bending can, in a particularly expedient manner, be effected in such a way that the application element is first withdrawn by a few millimeters from the housing and is then bent. In this state, the micro-brush is still protected by the housing so that no separate additional bending tool is needed. Pursuant to another particularly advantageous specific embodiment of the present invention, the constriction can be disposed just below a widened or thickened portion, the front abutment shoulder of which at the same time serves for introduction of the sealing mechanism. The widened portion then at the same time forms the transition between the grip and the shaft, and offers to the dentist an ergonomically favorable handling reliability that prevents him from inadvertently contacting the tip region of the application element that carries the reaction substance while he guides the application element.

Pursuant to a further advantageous specific embodiment, the grip, which is adjacent to the widened portion, can be provided with grooves or other suitable surface configurations that provide a favorable grip.

The inventive applicator kit can be produced decidedly economically as a single-dose unit, with the micro-brush preferably being made of polypropylene.

The inventive sealing mechanism fulfills a number of functions in a particularly expedient manner. On one hand, the base of the sealing mechanism, prior to use of the applicator, reliably seals against an inner annular bead of a housing. It is preferably made of a polymeric material that is somewhat softer than the material of the housing. At the same time, it serves for guiding the shaft of the application element, in which connection it is preferred that the friction between the shaft and the sealing mechanism on the one hand, and between the sealing mechanism and the housing on the other hand, also be great enough in the region of the upper overflow ring that the components of the inventive applicator kit do not inadvertently fall apart.

It is to be understood that prior to use the inventive applicator is accommodated in a suitable, preferably air tight, package so that also the reaction substance is not subjected to any environmental influences through the narrow gap, the ring of the sealing mechanism, and the shaft.

Further specific features of the present invention will be described in detail subsequently.

BRIEF DESCRIPTION OF THE DRAWINGS

The above objects, and other objects and advantages of the present invention, will appear more clearly from the following specification in conjunction with the accompanying schematic drawings, which show preferred embodiments of this invention.

DESCRIPTION OF PREFERRED EMBODIMENTS

Figure 1:
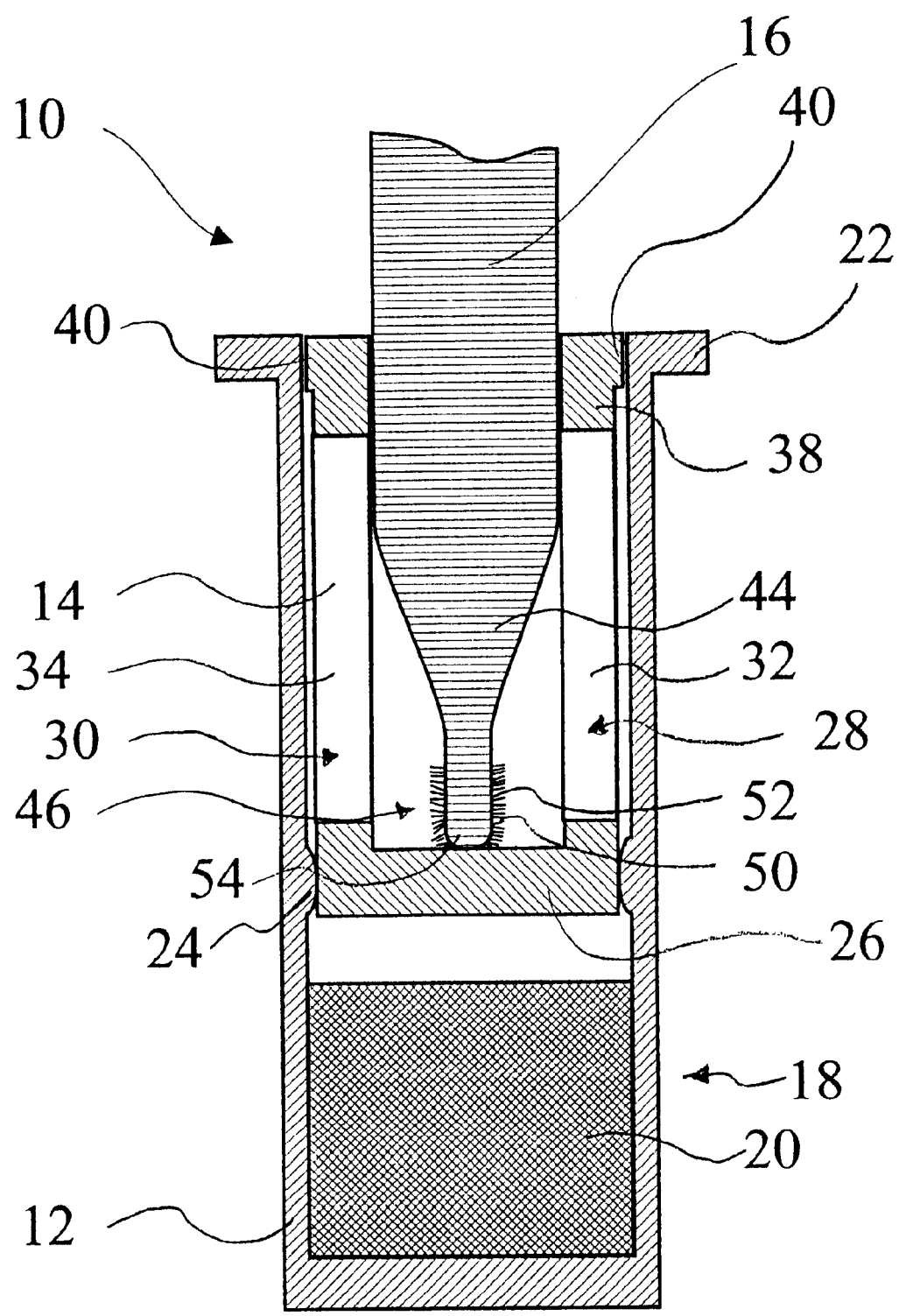
FIG. 1 is a cross-sectional view through one exemplary embodiment of an inventive applicator kit.

Referring now to the drawings in detail, the applicator kit 10 illustrated in FIG. 1 is provided with a housing 12 in which is guided an essentially cup-shaped sealing mechanism 14, which in turn accommodates an application element 16.

The lower region of the housing 12 is provided with a receiving portion 18 for a fluid or liquid 20. The housing 12 is also essentially cup-shaped and is provided at its upper end with a reinforcing rim 22 that is embodied as an outwardly directed collar. Somewhat less than half way along the housing 12 the latter is provided with an inwardly directed projected bead 24 that has an essentially convex configuration and serves for providing a seal against an outer surface of a disk shaped base 26 of the sealing mechanism 14.

For this purpose the base 26 of the sealing mechanism 14 is slightly oversized relative to the inner diameter of the bead 24. Pursuant to one particularly advantageous embodiment, the outer periphery of the base 26 is slightly concave so that a certain arresting function results for fixing the sealing mechanism 14 in a direction toward the top and the bottom.

The sealing mechanism 14 is provided above the base 26 and to the side with two rather large recessed areas or lateral opnings 28 and 30 that extend over nearly the entire height of the sealing mechanism 14. When the sealing mechanism 14 is pushed in, by applying force to the application element 16, the fluid 20 can easily and rapidly flow through the recessed areas 28 and 30, to wet the lower end of the applicator element 16.

To delimit the recessed areas 28 and 30, the sealing mechanism 14 is furthermore provided with two rods or supports 32 and 34 that connect the disc or plate-shaped base 26 of the sealing mechanism with a circular ring 38 which extends between the annular gap that exists between the application element 16 and the upper end of the housing 12.

The connection or termination ring 38 is provided with an annular guide projection in the form of an outwardly directed shoulder 40 having an outer diameter that is greater than an inner diameter of said ring and slightly less than an inner diameter of the housing. As a consequence of this construction, the sealing mechanism 14 is axially movably guided in the housing, wherein in order to overcome the sealing function of the sealing mechanism at the base 26, a certain amount of force must be applied.

Figure 1A:
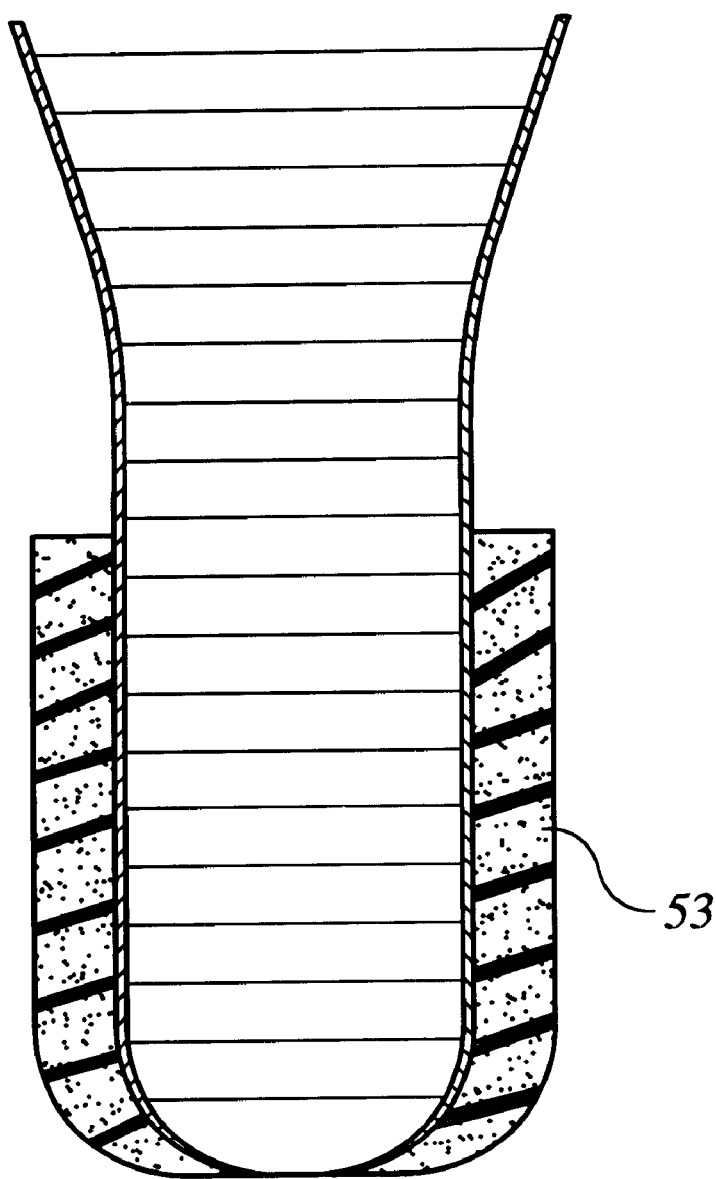
FIG. 1a is an enlarged view an application element provided with a sponge.

This force can inventively be applied via the application element 16. The application element has a grip area 42 shown in FIG. 2. Via a tapered area, the grip 42 merges with a shaft 44 that ends in a region 46 that is provided with micro hairs. This region forms an inventive application member 50, which in this embodiment is illustrated in the form of a micro-brush. In the illustrated embodiment, the micro-brush 50 is formed by a flocking, so that numerous, irregularly disposed brush hairs 52 extend outwardly. While a micro brush is shown in FIGS. 1, 2 and 3, a sponge 53 may be employed as shown in FIG. 1a.

The micro-haired region 46 ends in a rather blunt tip 54. This enables the transmission of force to the base 26 of the sealing mechanism 14, and hence the introduction of the sealing mechanism into the fluid receiving portion of the housing to cause fluid flow in a manner which should be apparent.

In the embodiment illustrated in FIG. 1, the brush hairs 52 are rather short. The length of the hairs affects the absorption or receiving capacity not only for the reaction substance 55, which is applied there as a deposited salt, but also for the fluid 20. This embodiment is suitable for applying particularly small quantities of adhesive.

Figure 2:
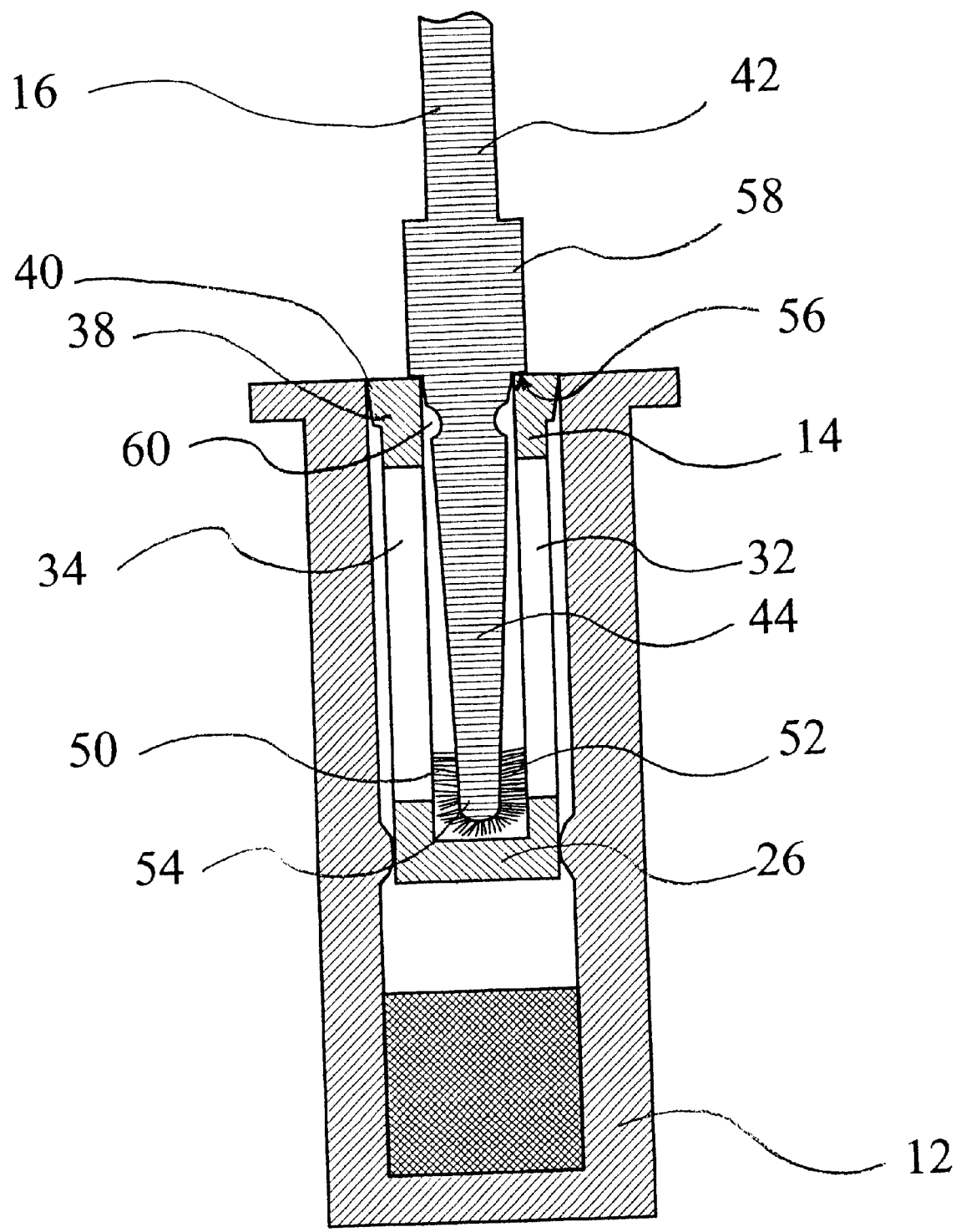
FIG. 2 is a cross-sectional view through a further exemplary embodiment of an inventive applicator kit.
Figure 3:
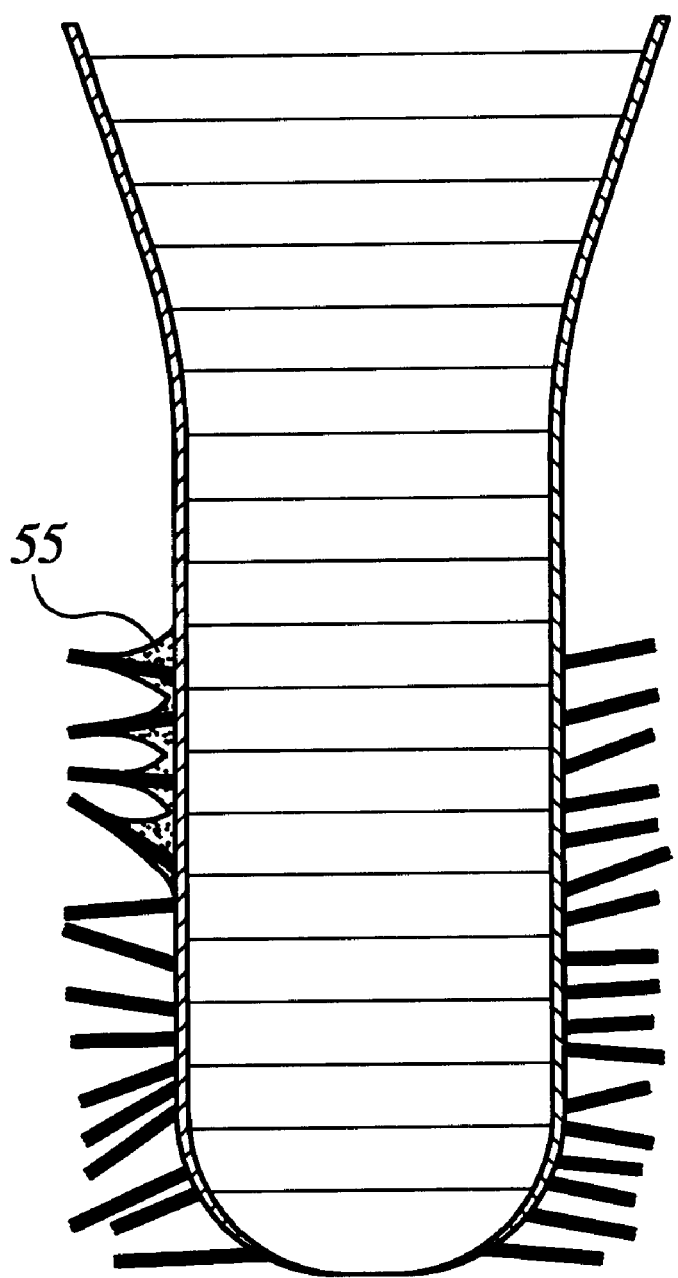
FIG. 3 is an enlarged view of a portion of FIG. 1 showing the reaction substance carried by the application member.

FIG. 2 shows a modified embodiment of the inventive applicator. Where applicable, the same reference numerals have been used for the same components and require no further explanation. In contrast to the embodiment of FIG. 1, the shaft 44 of the application element 16 in this embodiment has a conical shape. In addition, the brush hairs 52 are longer and extend to the supports 32, 34. Furthermore, in this embodiment the introduction of the sealing mechanism 14 is effected not via the tip 54 of the application element 16, but rather via an abutment shoulder 56 that is formed on a widened portion 58 that in this embodiment separates the grip 42 from the shaft 44 and is intended for abutment against the top of the ring 38 since the widened portion 58 has a diameter that is greater than an inner diameter of the ring 38.

Somewhat below the abutment shoulder 56 there is provided in this embodiment a constriction or groove 60 that offers the possibility of bending the shaft 44 relative to the grip 42. Due to the configuration of the application element 16, a plastic deformation is possible, whereby tests have shown that the shaft 44 springs back only somewhat relative to the grip 42 from the bent position.

The distance between the upper side of the base 26 and the upper side of the ring 38 is somewhat greater than the distance between the tip 54 and the abutment shoulder 56. This ensures that the micro-brush 50 can be entirely accommodated in the essentially cup-shaped sealing mechanism 14 without the brush hairs 52 getting bent at the base 26.

In this embodiment, the housing 12 is relatively stable, so that it can also endure rather rough handling. On the other hand, the plastic or polymeric material of the sealing mechanism 14 is much softer, so that the sealing function is ensured. Also with this embodiment the shoulder 40 is somewhat conical, so that there results a certain sealing function relative to the housing 12 and also the reaction substance on the micro-brush 50 is accommodated in a sealed manner.

Pursuant to a further modified embodiment, it is provided that the ring 38 has an inwardly directed bead that somewhat engages the constriction 60. As a consequence of this configuration, the application element 16 can be reliably supported in the sealing mechanism 14.

The following is a list of the process steps that are necessary for the conventional adhesive restorative dentistry. For the direct restoration with a composite filler, the following steps are required;

1. Remove decay.
2. Clean, dry and if necessary place an under-filling.
3. Etch dentine and enamel.
4. Apply Syntax-component with a brush.
5. Wait 20 seconds.
6. Blast with air.
7. Twenty second light polymerization.
8. Apply second layer as above.

9. Application of the composite and light hardening.

With the inventive applicator and the inventive method, it is possible to eliminate steps 5 to 7, and depending upon the application also step 8, so that the application process is accelerated and simplified, which is also an advantage with regard to failure reliability since each separate process step must be carried out with great care for a good restoration result. The specification incorporates by reference the disclosure of German priority document 199 56 705.0.

The present invention is, of course, in no way restricted to the specific disclosure of the specification and drawings, but also encompasses any modifications within the scope of the appended claims.

What is claimed is:

1. An applicator kit for applying a substance formed of a reaction substance and a fluid, which kit facilitates homogeneous mixing of said fluid with said reaction substance, which is easy to use, and which saves time in its use; the kit comprising:

an application element having a shaft, a grip area, and a working end;

an application member disposed at said working end of said application element and comprised of a deformable material;

a reaction substance carried by the application member which is activated by a low viscosity fluid;

a housing that surrounds said shaft of said application element as well as said application member, said housing being provided with a receiving portion; and said low viscosity fluid being normally maintained within said receiving portion;

wherein the application element, application member, reaction substance, housing and fluid are so arranged and constructed that when said application member is introduced into said fluid in the receiving portion, said homogeneous mixing of said fluid with the reaction substance takes place to activate the reaction substance.

2. An applicator kit according to claim 1, wherein said deformable material of said application member comprises a material that is significantly softer than dentine.

3. An applicator kit according to claim 1, wherein said deformable material of said application member is in the form of a sponge.

4. An applicator kit according to claim 1, wherein said deformable material of said application member is in the form of a micro-brush.

5. An applicator kit according to claim 1, wherein a periphery of said shaft of said application element is provided with a groove via which said shaft is bendable.

6. An applicator kit according to claim 1, wherein said reaction substance is at least a catalyst that is applied to said application member.

7. The applicator kit according to claim 1, wherein said viscosity of said fluid is in the range of 10 and 500,000 mPa.

8. The applicator kit according to claim 7, wherein said viscosity of said fluid is in the range of 1,000 and 100,000 mPa.

9. The applicator kit according to claim 8, wherein said viscosity of said fluid is in the range of 10,000 and 50,000 Mpa.

10. An applicator kit according to claim 1 further comprising a sealing mechanism that is guidingly accommodated in said housing, and wherein said sealing mechanism, in a rest position, seals said receiving portion for said fluid.

11. An applicator kit according to claim 10, wherein said sealing mechanism is movable via application of force to the application element so as to overcome the sealing as the sealing mechanism is introduced into the receiving portion.

12. An applicator kit according to claim 11, wherein said sealing mechanism is essentially cup-shaped, and wherein said application member has a blunt tip for enabling the transition force to said sealing mechanism.

13. An applicator kit according to claim 10, wherein said sealing mechanism is provided with a disk shaped>base and at an opposite end with a ring that is interconnected to said base by at least two spaced apart supports which define at least two lateral openings via which said application member, after the sealing mechanism is introduced into the receiving portion, is wetted by said fluid.

14. An applicator kit according to claim 13, wherein a widened portion is provided between said shaft and said grip area of said application element, and wherein said widened portion has a diameter that is greater than an inner diameter of said ring.

15. An applicator kit according to claim 14, wherein a distance between an upper side of said base an upper side of and said ring is somewhat greater than a distance between a tip of said application member and an end of said widened portion.

16. An applicator kit according to claim 13, wherein said deformable material of said application member is in the form of a micro-brush, and wherein the brush hairs of said micro-brush extend to said supports of said sealing mechanism.

17. An applicator kit according to claim 13, wherein an inner surface of said housing is provided with a projecting bead, and a seal is formed between said bead and an outer surface of said sealing mechanism.

18. An applicator kit according to claim 10, wherein said application member is in the form of a micro-brush flocked with brush hairs and having a blunt tip.

19. An applicator kit according to claim 10, wherein an upper end of said sealing mechanism remote from a base thereof is provided with an annular guide projection having an outer diameter slightly less than an inner diameter of said housing, so that the sealing mechanism may move relative to said housing with the sealing mechanism being guided in the housing.

\* \* \* \* \*

UNITED STATES PATENT AND TRADEMARK OFFICE
CERTIFICATE OF CORRECTION

PATENT NO.  : 6,450,717 B1
DATED       : September 17, 2002
INVENTOR(S) : Ulrich Salz et al.

It is certified that error appears in the above-identified patent and that said Letters Patent is hereby corrected as shown below:

<u>Column 8,</u>
Line 3, "Mpa" should be --mPa --;
Line 13, -- function -- should be inserted after "sealing";
Line 18, change "transition" to -- transmission of --;
Line 20, change "shaped>base" to -- shaped base --;
Line 32, change "an" second occurrence to -- and --.

Signed and Sealed this

Fourth Day of March, 2003

JAMES E. ROGAN
*Director of the United States Patent and Trademark Office*